(12) United States Patent
Tsao

(10) Patent No.: US 9,339,665 B2
(45) Date of Patent: May 17, 2016

(54) ULTRASONIC WAVE HEATING INSTRUMENT

(71) Applicant: Minhao Tsao, Guangdong (CN)

(72) Inventor: Minhao Tsao, Guangdong (CN)

( * ) Notice: Subject to any disclaimer, the term of this patent is extended or adjusted under 35 U.S.C. 154(b) by 48 days.

(21) Appl. No.: 14/370,216

(22) PCT Filed: Sep. 27, 2012

(86) PCT No.: PCT/CN2012/001321
§ 371 (c)(1),
(2) Date: Jul. 1, 2014

(87) PCT Pub. No.: WO2013/104094
PCT Pub. Date: Jul. 18, 2013

(65) Prior Publication Data
US 2014/0336541 A1  Nov. 13, 2014

(30) Foreign Application Priority Data
Jan. 11, 2012  (CN) ................... 2012 2 0010620 U

(51) Int. Cl.
*A61N 7/02* (2006.01)
*A61N 7/00* (2006.01)
*A61F 7/00* (2006.01)
*A61H 7/00* (2006.01)
*A61H 23/02* (2006.01)

(52) U.S. Cl.
CPC ... *A61N 7/02* (2013.01); *A61F 7/00* (2013.01); *A61H 7/003* (2013.01); *A61H 7/007* (2013.01); *A61H 23/0236* (2013.01); *A61N 7/00* (2013.01); *A61F 2007/0052* (2013.01); *A61H 2201/0207* (2013.01); *A61H 2201/0228* (2013.01); *A61N 2007/0034* (2013.01)

(58) Field of Classification Search
CPC ............. A61F 2007/0052; A61F 7/00; A61H 2201/0207; A61H 2201/0228; A61H 23/0236
See application file for complete search history.

(56) References Cited

U.S. PATENT DOCUMENTS

| | | | |
|---|---|---|---|
| 7,090,649 B2 * | 8/2006 | Kang ................. | A61H 23/0245 601/15 |
| 2004/0171970 A1 * | 9/2004 | Schleuniger ........... | A61B 8/546 601/2 |
| 2007/0198004 A1 * | 8/2007 | Altshuler ........... | A46B 15/0036 606/9 |

\* cited by examiner

Primary Examiner — Baisakhi Roy
(74) *Attorney, Agent, or Firm* — Leong C. Lei

(57) ABSTRACT

A ultrasonic wave heating instrument includes a housing inside which a ultrasonic wave emitting circuit in electric connection with a power source and a ultrasonic oscillating sheet in electric connection with said circuit are configured, and a ceramic massage head is configured on the housing. The ultrasonic wave generated from the ultrasonic oscillating sheet is passed through the ceramic massage head to act on human bodies. Besides, a switch is configured between the power source and ultrasonic wave emitting circuit. Furthermore, a heating membrane in electric connection with the power source is configured inside the housing, and the heat emitted from the heating membrane is passed through the ceramic massage head to act on human bodies.

2 Claims, 2 Drawing Sheets

1

ULTRASONIC WAVE HEATING INSTRUMENT

TECHNICAL FIELD OF THE INVENTION

The present invention relates to a heater, and more particularly to a ultrasonic wave heating instrument.

DESCRIPTION OF THE PRIOR ART

Ultrasonic wave refers to mechanical vibration wave, which is more than twenty thousand hertz in frequency and cannot be heard by normal persons. The ultrasonic wave has a mechanical function, tepid function and chemical function; it has an unimaginable beauty effect comparing with normal face beautifying instruments when it is used on human's faces to carry out beauty care. Infrared light good for human bodies can be generated after heat is acted through a ceramic massage head. Thus, a ultrasonic wave heating instrument using the two above-mentioned manners synthetically to carry out beauty treatment.

SUMMARY OF THE INVENTION

To overcome the insufficiency of the current technology, the present invention provides an instrument generating infrared light to carry out beauty treatment by a ultrasonic oscillating sheet generating ultrasonic wave to pass through a ceramic massage head.

The present invention proposes a ultrasonic wave heating instrument including a housing inside which a ultrasonic wave emitting circuit in electric connection with a power source and a ultrasonic oscillating sheet in electric connection with the circuit are configured. Furthermore, a ceramic massage head is configured on the housing, thereby the ultrasonic wave generated from the ultrasonic oscillating sheet being passed through the ceramic massage head to act on human bodies. In addition, a switch is configured between the power source and the ultrasonic wave emitting circuit. Furthermore, a heating membrane, which is in electric connection with the power source, is configured inside the housing, and heat emitted from the heating membrane is passed through the ceramic massage head to act on human bodies.

The ceramic massage head is engaged with the housing through an annular cover.

The beneficial effects of the present invention are in that the present invention acts on a face to cause skin cells to vibrate by means of the mechanical function of ultrasonic wave to generate a very small massage function thereon to change cell capacity. Thereupon, the part circulation of blood and lymph can be improved, cell permeability is enhanced, the metabolism and regenerative capability of skin tissue is increased, the skin tissue is softened, and nervous system and cell function are stimulated, allowing the skin to be full of luster and elasticity; the temperature of skin surface can be increased by means of the tepid function of ultrasonic wave, allowing the circulation of blood to be speeded, the nutrient of skin cells to be increased, hypertarachia to be lowered down, thereby achieving pain control, and spasmodic muscle fibers to be relaxed, thereby achieving spasm relaxation function. The heat of ultrasonic wave is endogenous heat, where 79%~82% thereof is transported by the self-acting zone, and 18%~21% thereof is dispersed into adjacent tissue by means of heat conduction. Therefore, a patient feels no obvious heat. Furthermore, catalytic ability can be strengthened and the metabolism of skin cells speeded by mean of the chemical function of ultrasonic wave, allowing pH value of tissue to be changed toward alkalinity, the acidosis and pain yielded from dermatitis to be lightened. Furthermore, ultrasonic wave can enhance the permeability of cell membrane, allowing the depropagation of nutrients and medicines, facilitating the absorption of nutrients by skin, and penetration of medicines into bacterial bodies, thereby increasing sterilization capability. In addition, the ceramic massage head of the present invention is made from ceramic material; the heat function of the ceramic massage head allows it to emit far-infrared rays with a longer wavelength suitable of human being while passing through a heating membrane bodies comparing with metal material. Generally speaking, far-infrared light has a stronger osmotic force and radiation force, provided with a noticeable temperature control effect and resonance effect, easy to be absorbed by bodies and therefore changed to the internal energy of the bodies. Far-infrared rays allows the water molecules to generate resonance after being absorbed by the human bodies, allowing the water molecules to be activated and thereby to strengthen coupling force among them and activate large biological molecules such proteins, enabling the cells of organism bodies to be in the highest vibration energy state. Therefore, the far-infrared rays being acted on human bodies enables capillary blood vessels to be expanded, blood circulation to be promoted, and metabolism among tissues to be strengthened, thereby achieving a beauty care function. Conclusively, the present invention achieves a better beauty care effect through the double function of far-infrared light and ultrasonic wave acted upon human bodies.

The specific functions of the present invention are described as the following: Softening thrombus, eliminating the "red face", applied on facial erythrocyte, erythema caused by tiny blood vessels deformation of faces, blood circulation disorder, and facial redness or rosacea due to infection caused by mites.

BRIEF DESCRIPTION OF THE DRAWINGS

The present invention can be more fully understood by reference to the following description and accompanying drawings, in which.

DETAILED DESCRIPTION OF THE PREFERRED EMBODIMENTS

Figure 1:
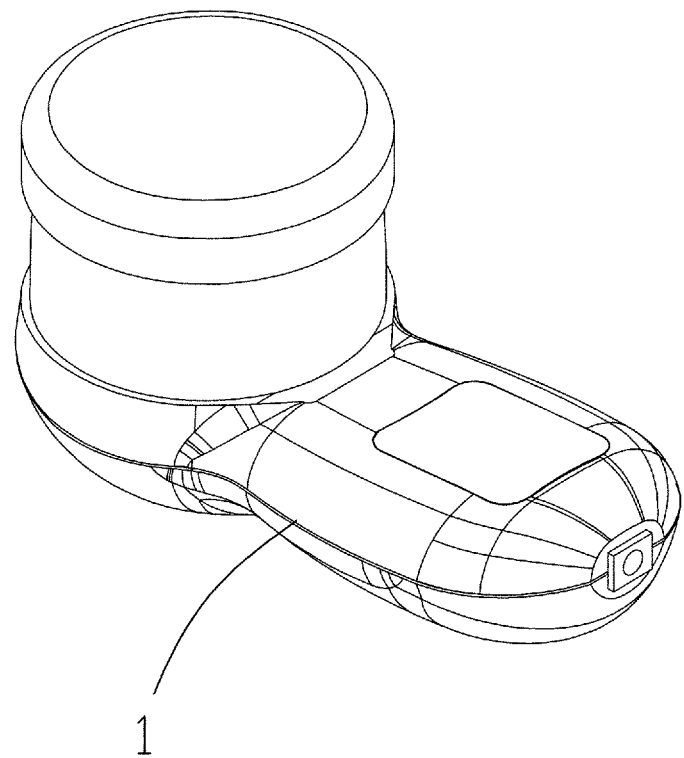
FIG. 1 is a perspective view of a ultrasonic wave heating instrument according to the present invention.
Figure 2:
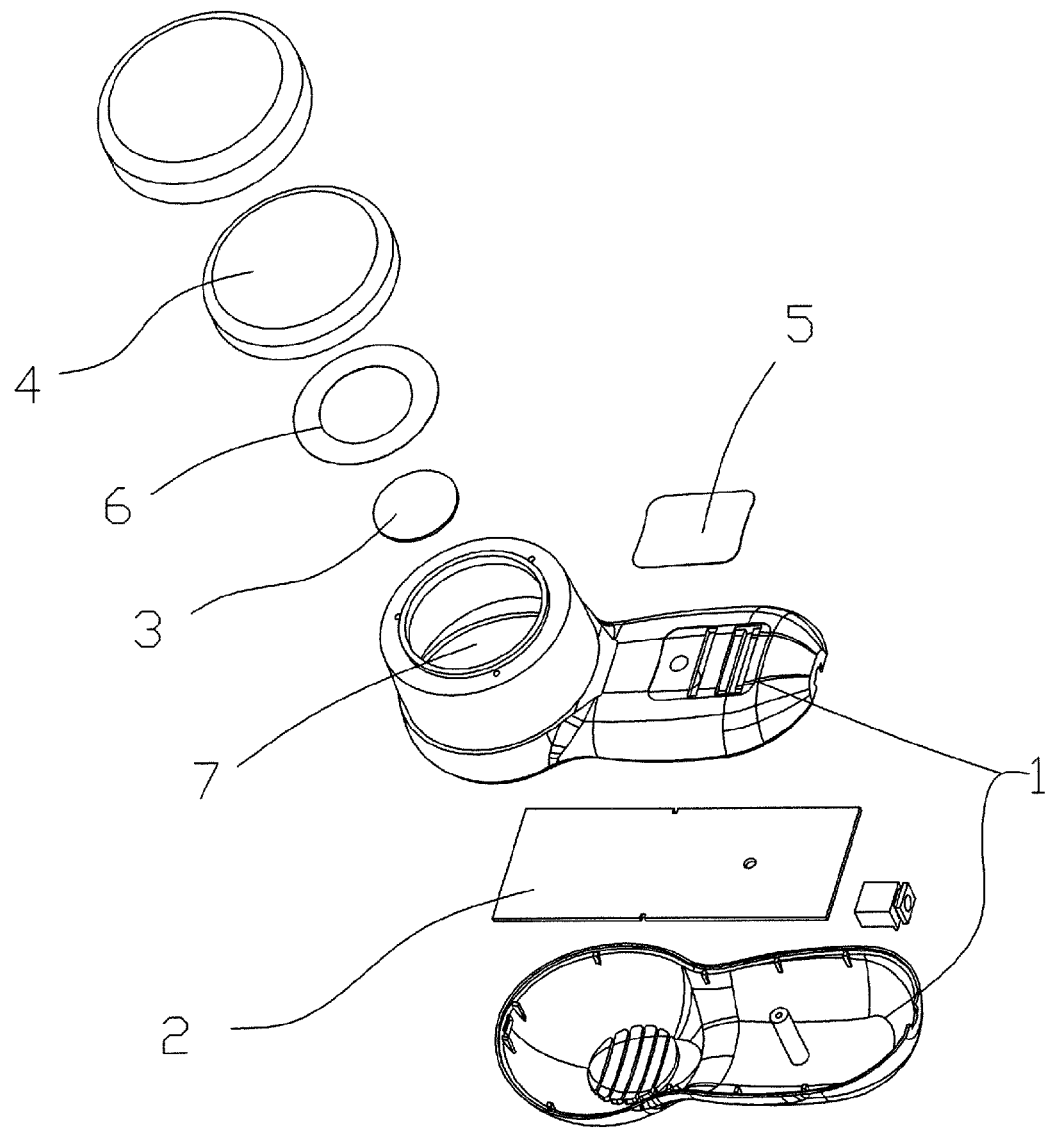
FIG. 2 is an exploded view of the ultrasonic wave heating instrument according to the present invention.

Referring to FIGS. 1 and 2, the present invention proposes a ultrasonic wave heating instrument, including a housing 1 inside which a ultrasonic wave emitting circuit 2 in electric connection with a power source and a ultrasonic oscillating sheet 3 in electric connection with the circuit 2 are configured. Furthermore, a ceramic massage head 4 is configured on the housing 1, where the ultrasonic wave generated from the ultrasonic oscillating sheet 3 is passed through the ceramic massage head 4 to act on human bodies. In addition, a switch 5 is configured between the power source and ultrasonic wave emitting circuit 2. A heating membrane 6 in electric connection with the power source is configured inside the housing 1, where the heat emitted from the heating membrane 6 is passed through the ceramic massage head 4 to act on human bodies.

In the present embodiment, an accommodation chamber 7, inside which the ultrasonic oscillating sheet 3 and heating membrane 6 are mounted, is disposed within the head portion of the housing 1, and the ceramic massage head 4 is mounted on the mouth portion of the accommodation chamber 7. Furthermore, for the convenient and solid configuration of the ceramic massage head on the housing 1, the ceramic massage head 4 is mounted on the housing 1 through an annular cover.

Although a particular embodiment of the present invention have been shown and described, it should be understood that the above discussion is not intended to limit the present invention to this embodiment. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

I claim:

1. An ultrasonic wave heating instrument, comprising a housing, an ultrasonic wave emitting circuit in electric connection with a power source and an ultrasonic oscillating sheet in electric connection with said circuit being configured inside said housing, a ceramic massage head being configured on said housing and separate from said ultrasonic oscillating sheet, ultrasonic wave generated from said ultrasonic oscillating sheet being passed through said ceramic massage head adapted to act on human bodies, a switch being configured between said power source and ultrasonic emitting circuit, a heating membrane being configured inside said housing and separate from said ultrasonic oscillating sheet, said heating membrane being in electric connection with said power source, and heat emitted from said heating membrane being passed through said ceramic massage head to be converted into infrared ray adapted to act on human bodies.

2. The instrument according to claim 1, wherein said ceramic massage head is mounted on said housing through an annular cover.

* * * * *